(12) United States Patent
Poornaprajna et al.

(10) Patent No.: US 7,230,120 B2
(45) Date of Patent: Jun. 12, 2007

(54) AMORPHOUS HMG-COA REDUCTASE INHIBITORS OF DESIRED PARTICLE SIZE

(75) Inventors: Acharya Poornaprajna, Karnataka (IN); Joy Mathew, Karnataka (IN); Ravindra Chandrappa, Karnataka (IN); Madhavan Sridharan, Karnataka (IN); Sambasivam Ganesh, Karnataka (IN)

(73) Assignee: Biocon, Bangalore (IN)

( * ) Notice: Subject to any disclaimer, the term of this patent is extended or adjusted under 35 U.S.C. 154(b) by 202 days.

(21) Appl. No.: 10/483,553

(22) PCT Filed: Mar. 18, 2002

(86) PCT No.: PCT/IN02/00045

§ 371 (c)(1),
(2), (4) Date: Jan. 12, 2004

(87) PCT Pub. No.: WO03/078379

PCT Pub. Date: Sep. 25, 2003

(65) Prior Publication Data

US 2004/0186162 A1 Sep. 23, 2004

(51) Int. Cl.
*C07D 207/335* (2006.01)
(52) U.S. Cl. ..................................... 548/537
(58) Field of Classification Search ............. None
See application file for complete search history.

(56) References Cited

U.S. PATENT DOCUMENTS

| | | | | |
|---|---|---|---|---|
| 5,273,995 | A * | 12/1993 | Roth | 514/422 |
| 6,274,740 | B1 | 8/2001 | Lin et al. | |
| 6,528,661 | B2 | 3/2003 | Niddam et al. | |
| 6,646,133 | B1 * | 11/2003 | Greff et al. | 548/537 |
| 2002/0099224 | A1 | 7/2002 | Niddam et al. | |
| 2003/0114685 | A1 | 6/2003 | Niddam-Hildesheim et al. | |
| 2003/0175338 | A1 | 9/2003 | Singh et al. | |
| 2005/0119343 | A1 | 6/2005 | Tillyer et al. | |

FOREIGN PATENT DOCUMENTS

| | | |
|---|---|---|
| WO | WO 97/03958 | 2/1997 |
| WO | WO 97/03960 | 2/1997 |
| WO | WO 00/53566 | 9/2000 |
| WO | WO0053566 | 9/2000 |
| WO | WO 01/10813 | 2/2001 |
| WO | WO 01/28999 * | 4/2001 |
| WO | WO 01/42209 | 6/2001 |
| WO | WO 02/43667 A2 | 6/2002 |
| WO | WO 03/004450 A1 | 1/2003 |
| WO | WO 03/004455 A2 | 1/2003 |
| WO | WO 03/004456 | 1/2003 |
| WO | WO 03/016317 | 2/2003 |

OTHER PUBLICATIONS

International Search Report for corresponding PCT application PCT/IN02/00045 (WO 03/078379).

Oehrlein R et al., "Chemoenzymatic approach to statin side-chain building blocks" Advanced Synthesis Catalysis (2003), 345 (6+7), 713-715.

Woo et al., "Atorvastatin, an HMG-CoA reductase inhibitor and effective lipid-regulating agent. Part III. Syntheses of [2H5]-, [13C8], and [13C7, 15N] atorvastatin and their application in metabolic and pharmacokinetic studies", Journal of Labeled Compounds Radiopharmaceuticals (1999), 42(2), 135-145.

Lee et al., "Atorvastatin, an HMG-CoA reductase inhibitor and effective lipid-regulating agent. Part II. Synthesis of side chain-labeled [14C] atorvastatin", Journal of Labeled Compounds Radiopharmaceuticals (1999), 42(2), 129-133.

Woo et al., "Atorvastatin, an HMG-CoA reductase inhibitor and effective lipid-regulating agent. Part I. Synthesis of ring-labeled [14C] atorvastatin", Journal of Labeled Compounds Radiopharmaceuticals (1999), 42(2), 121-127.

Radl et al., "An improved synthesis of 1,1-dimethylethyl-6-cyanomethyl-2,2-dimethyl-1,3-dioxane-4-acetate, a key intermediate for atorvastatin synthesis", Tetrahedron Letters (2002), 43(11), 2087-2090.

Manzoni et al., "Biosynthesis and biotechnological production of statins by filamentous fungi and application of these cholesterol-lowering drugs", Applied Microbiology and Biotechnology (2002), 58(5), 555-564.

Roth, Bruce D., "The discovery and development of atorvastatin, a potent novel hypolipidemic agent", Progess in Medicinal Chemistry (2002), 40, 1-22.

Wierzbicki, Anthony S., "Atorvastatin", Expert Opinion on Pharmacotherapy (2001), 2(5), 819-830.

Graul et al., "Atorvastatin calcium", Drugs of the future (1997), 22(9), 956-968.

Baumann et al., "The convergent synthesis of CI-981, an optically active, highly potent, tissue-selective inhibitor of HMG-CoA reductase", Tetrahedron Letters (1992), 33(17), 2283-2284.

* cited by examiner

*Primary Examiner*—Kamal A. Saeed
*Assistant Examiner*—Andrew B. Freistein
(74) *Attorney, Agent, or Firm*—Andrea L.C. Robidoux; Choate, Hall & Stewart LLP

(57) ABSTRACT

In one aspect, the invention provides a process for the preparation of an amorphous HMG-CoA reductase inhibitor and hydrates thereof of desired particle size, which comprises: dissolving the HMG-CoA reductase inhibitor in a hydroxylic solvent, and removing the solvent by freeze-drying.

5 Claims, 2 Drawing Sheets

AMORPHOUS HMG-COA REDUCTASE INHIBITORS OF DESIRED PARTICLE SIZE

PRIORITY CLAIM

The present application claims the benefit under 35 U.S.C. § 371 of International Application No.: PCT/IN02/00045 (published PCT Application No. WO 02/057274), filed Mar. 18, 2002, the entire contents of this application is hereby incorporated herein by reference.

FIELD OF THE INVENTION

The present invention relates to a process for the production of amorphous HMG-CoA reductase inhibitors of desired particle size.

BACKGROUND OF THE INVENTION

Lovastatin, pravastatin, simvastatin, mevastatin, atorvastatin, fluvastatin, cervastatin and derivatives and analogs thereof are known as HMG-CoA reductase inhibitors and are used as antihypercholesterolemic agents. The majority of these inhibitors are produced by fermentation using microorganisms of species belonging to the *Aspergillus, Monascus, Nocardia, Amycolatopsis, Mucor* or *Penicillium* genus. Some inhibitors are the fermentation products themselves, or are obtained by treating the fermentation products using chemical methods.

The present invention relates to amorphous form HMG-CoA reductase inhibitors, useful as a pharmaceutical substance, and to a method for production and isolation thereof. HMG-CoA reductase inhibitors, are used for the treatment of hyperlipidemia and hypercholesterolemia, risk factors for arteriosclerosis and coronary heart disease.

U.S. Pat. No. 5,273,995, describes that the R-form of the ring opened acid of the atorvastatin lactone form inhibits the biosynthesis of cholesterol. Atorvastatin in its calcium salt form, i.e. amorphous [R—(R*, R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt (2:1), is discussed in the literature.

U.S. Pat. Nos. 5,003,080; 5,097,045; 5,103,024; 5,124,482; 5,149,837; 5,248,793; 5,280,126; 5,342,952, which are herein incorporated by reference, describe various processes and key intermediates for preparing atorvastatin calcium.

However, the processes mentioned in the above patents do not produce atorvastatin calcium in its amorphous form consistently. Often a mixture of crystalline and amorphous form is obtained which is not suitable for filtration and drying and therefore they are not a desirable processes for large-scale production.

PCT application WO 97/03959, discloses novel crystalline forms of atorvastatin calcium designated as Form I, Form II, and Form IV and a method for their preparation. PCT application WO 97/03960 describes a procedure for converting the crystalline form of atorvastatin to the amorphous form.

The process described in the later mentioned PCT application involves dissolving the crystalline atorvastatin (Form-I) in a non hydroxylic solvent like tetrahydrofuran or mixtures of tetrahydrofuran and toluene, followed by removal of the solvents under high temperature (about 90° C.) and high vacuum (about 5 mm). This process may not be suitable on a large scale as the conditions used for drying may lead to degradation of the product.

PCT application WO 00/71116 claims a process for the preparation of amorphous atorvastatin calcium where the crystalline form is dissolved in a non-hydroxilic solvent, treated with a non-polar hydrocarbon anti-solvent, and results in the amorphous form when the solvent in removed.

Pravastatin was first reported as a metabolite of compactin in U.S. Pat. No. 346,227. PCT Application WO01/43723 describes certain novel forms of pravastatin which are characterized by X-Ray patterns.

SUMMARY OF THE INVENTION

It is desirable to have a process which provides amorphous HMG-CoA reductase inhibitor using a procedure that may be readily scaled up to a commercial scale. The present invention describes a process ideal for large scale production of amorphous HMG-CoA reductase inhibitor.

The present invention provides in one aspect, a process for the preparation of amorphous HMG-CoA reductase inhibitor and hydrates thereof of desired particle size, which comprises:

(i) dissolving a heterogeneous mixture of HMG-CoA reductase inhibitor in a hydroxylic solvent and (ii) removing the solvent to obtain an amorphous HMG-CoA reductase inhibitor.

The process further comprises (iii) subjecting the amorphous HMG-CoA reductase inhibitor to milling.

In one embodiment, the solvent is may be removed by freeze drying or spray drying.

In another embodiment, the amorphous HMG-CoA reductase inhibitor has a particle size of 1 to 150 microns.

In yet another embodiment, the hydroxylic solvent solvent is methanol.

In a further embodiment, the HMG-CoA reductase inhibitor is a statin, preferably, atorvastatin or pravastatin having a particle size of 1 to 150 microns.

There are major advantages of the process of the present invention compared to the prior art processes. These include, for example, that the process of the present invention produces amorphous HMG-CoA reductase inhibitor consistently, results in the final product of desired particle size, avoids the necessity to remove solvents, results in simpler and faster filtration, is easy to operate on large-scale, and/or avoids the use of hydrocarbons.

Thus, in one aspect, the present invention provides a simple and novel process for the preparation of amorphous atorvastatin calcium and hydrates thereof. In certain embodiments, the starting material used in the present invention comprises a mixture of both amorphous and crystalline forms, henceforth referred to as heterogeneous mixture.

Figure 1:
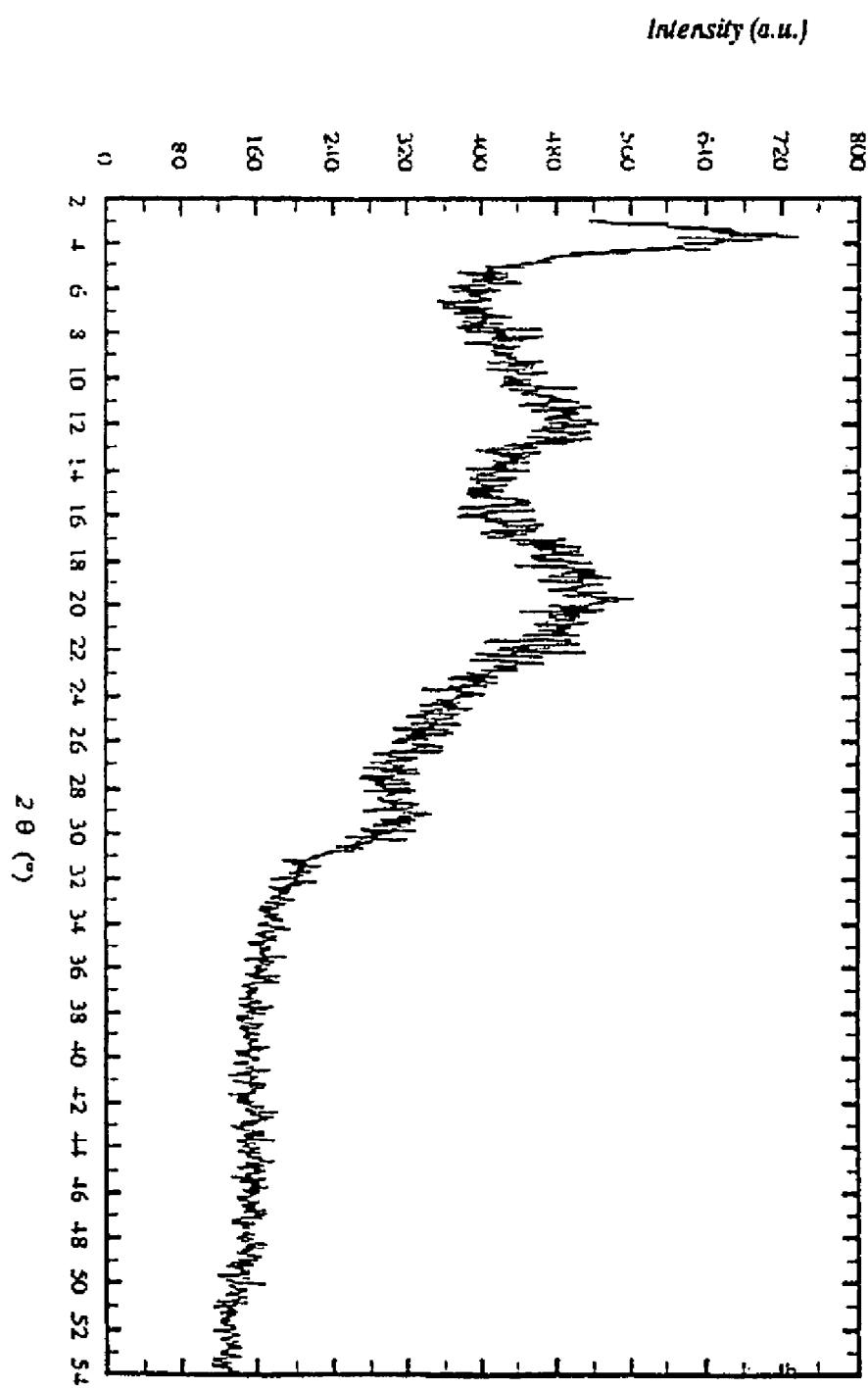
FIG. 1 is an exemplary diffractogram of amorphous atorvastatin calcium. The horizontal axis represents 2 and the vertical axis corresponds to peak intensity.

The present invention is illustrated by the following examples, but is not limited by them.

DETAILED DESCRIPTION OF CERTAIN PREFERRED EMBODIMENTS OF THE INVENTION

There are major advantages of the process of the present invention compared to the prior art processes. These include, for example, that the process of the present invention produces amorphous HMG-CoA reductase inhibitor consistently, results in the final product of desired particle size, avoids the necessity to remove solvents, results in simpler and faster filtration, is easy to operate on large-scale, and/or avoids the use of hydrocarbons.

Thus, in one aspect, the present invention provides a simple and novel process for the preparation of amorphous atorvastatin calcium and hydrates thereof. In certain embodiments, the starting material used in the present invention comprises a mixture of both amorphous and crystalline forms, henceforth referred to as heterogeneous mixture.

The illustrated embodiments have been set forth only for the purposes of example and should not be taken as limiting the invention. Therefore, it should be understood that within the scope of the appended claims, the invention may be practiced other than specifically described herein.

EXAMPLE 1

[R—(R*,R*)]-2-(4-fluorophenyl)-β,δ-dihydroxy-5-(1-methylethyl)-3-phenyl-4-[(phenylamino)carbonyl]-1H-pyrrole-1-Heptanoic Acid Hemi Calcium Salt (Amorphous Atorvasatin Calcium)

A heterogeneous mixture of atorvastatin (5 g) was added to methanol (100 ml) and the resulting reaction mixture was freeze dried to afford amorphous atorvastatin.

The particle size as measured by a malvern particle size analyser gave the following pattern:

| | |
|---|---|
| $D_{10}$ | 3 microns |
| $D_{50}$ | 9 microns |
| $D_{90}$ | 16 microns |

EXAMPLE 2

[1S-([1α(β*δ*)2α, 6α, 8B(R*), 8aα]]-1,2,6,7,8,8a-hexahydro-β,δ,6-trihydroxy-2-methyl-8-(2-methyl-1-oxobutoxy)-1-naphthalene heptanoic Acid Sodium Salt (Amorphous Pravastatin)

A heterogeneous mixture of pravastatin sodium (5 g) was added to methanol (100 ml) and the resulting reaction mixture was spray dried to afford amorphous pravastatin sodium. The amorphous pravastatin sodium so obtained was milled using an air jet mill.

The particle size as measured by a malvern particle size analyser gave the following pattern:

| | |
|---|---|
| D10 | 3 micron |
| D50 | 11 micron |
| D90 | 19 micron |

EXAMPLE 3

[1S-([1α(β*,δ*) 2α, 6α, 8B(R*),8aα]]-1,2,6,7,8,8a-hexahydro-β,6-trihydroxy-2-methyl-8-(2-methyl-1-oxobutoxy)-1-naphthalene heptanoic acid sodium salt (Amorphous Pravastatin)

A heterogeneous mixture of pravastatin sodium (5 g) was added to water (100 ml) and the resulting reaction mixture was spray dried to afford amorphous pravastatin sodium. The amorphous pravastatin sodium so obtained was milled using an air jet mill. The particle size as measured by a malvern particle size analyser gave the following pattern:

| | |
|---|---|
| D10 | 2 micron |
| D50 | 4 micron |
| D90 | 10 micron |

EXAMPLE 4

[R-(R*,R*)]-2-(4-fluorophenyl)-β, δ-dihydroxy-5-(1-methylethyl)-3-phenyl-4-[(phenylamino)carbonyl]-1H-pyrrole-1-heptanoic acid hemi calcium salt (Amorphous Atorvasatin calcium)

A heterogeneous mixture of atorvastatin (5 g) was added to methanol (100 ml) and the resulting reaction mixture was spray dried to afford amorphous atorvastatin.

The particle size as measured by a malvern particle size analyser gave the following pattern:

| | |
|---|---|
| $D_{10}$ | 1 microns |
| $D_{50}$ | 6 microns |
| $D_{90}$ | 11 microns |

EXAMPLE 5

[1S-([1α(β*,δ*)2α, 6α,8B(R*),8aα[ ]-1,2,6,7,8,8a-hexahydro-β,δ,6-trihydroxy-2-methyl-8-(2-methyl-1-oxobutoxy)-1-naphthalene heptanoic acid sodium salt (Amorphous Pravastatin)

A heterogeneous mixture of pravastatin sodium (5 g) was added to methanol (100 ml) and the resulting reaction mixture was freeze dried to afford amorphous pravastatin sodium. The amorphous pravastatin sodium so obtained was milled using an air jet mill.

The particle size as measured by a malvern particle size analyser gave the following pattern:

| | |
|---|---|
| D10 | 2 micron |
| D50 | 8 micron |
| D90 | 16 micron |

Figure 2:
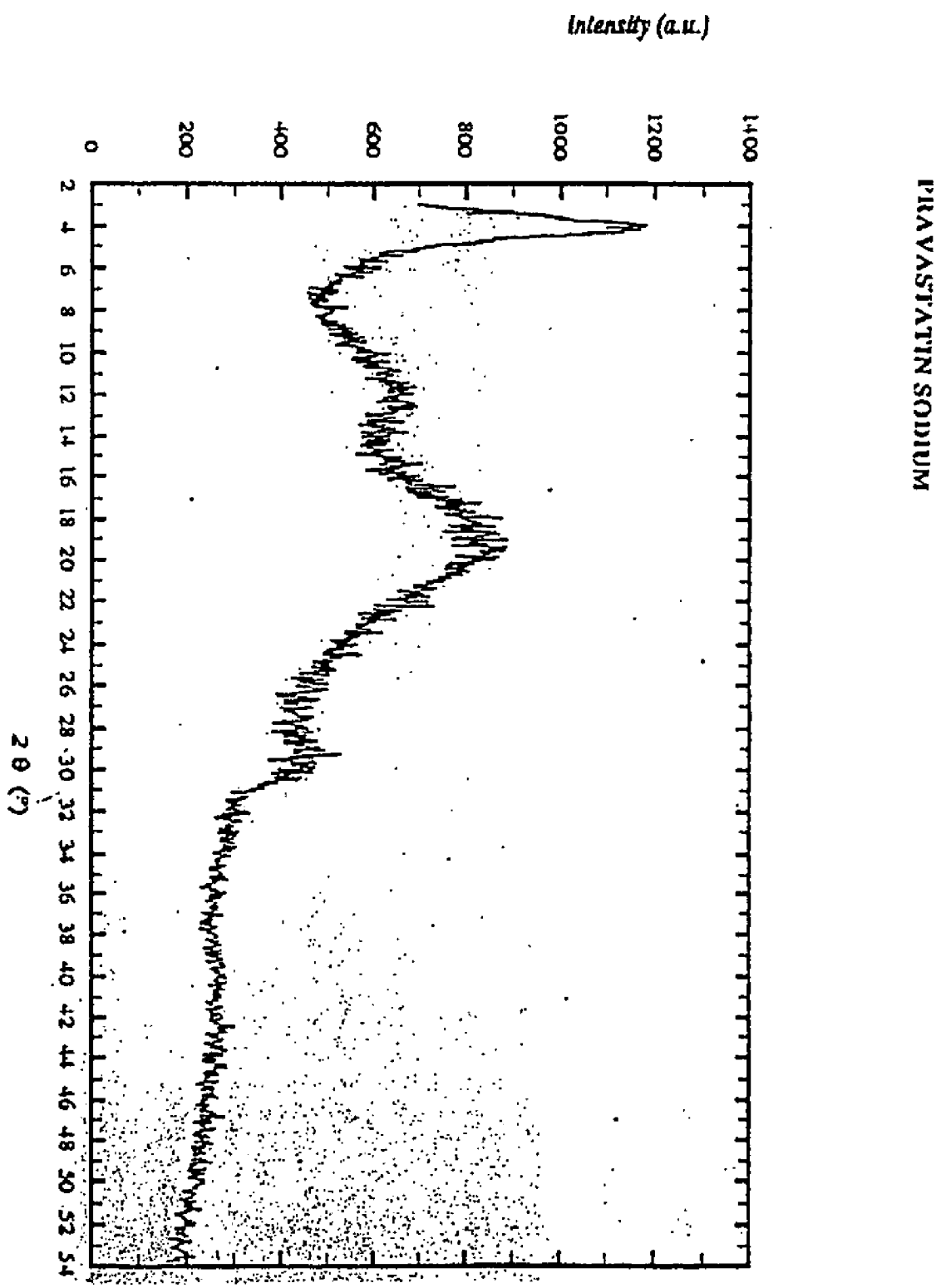
FIG. 2 is an exemplary diffractogram of amorphous pravastatin. The horizontal axis represents 2 and the vertical axis corresponds to peak intensity.

FIG. 1 and FIG. 2 depicts x-ray powder diffractions demonstrating the amorphous nature of the products (atorvastatin and provastatin, respectively).

We claim:

1. A process for the preparation of amorphous HMG-CoA reductase inhibitor selected from Atorvastatin, and hydrates thereof, of particle size of 1 to 150 microns, comprising:
   dissolving a heterogeneous mixture of the HMG-CoA reductase inhibitor in a hydroxylic solvent; and
   removing the solvent to obtain amorphous HMG-CoA reductase inhibitor, wherein the solvent is removed by spray drying or freeze drying.

2. The process of claim 1, further comprising subjecting the amorphous HMG-CoA reductase inhibitor to milling.

3. The process of claim 1, wherein the solvent is removed by spray drying.

4. The process of claim 1, wherein the hydroxylic solvent is methanol.

5. The process of claim 1, wherein the solvent is removed by freeze drying.

* * * * *